US009388474B2

(12) United States Patent
Kubota et al.

(10) Patent No.: US 9,388,474 B2
(45) Date of Patent: Jul. 12, 2016

(54) METHOD FOR DETECTING TOXIN-PRODUCING *CLOSTRIDIUM DIFFICILE*

(75) Inventors: Hiroyuki Kubota, Kofu (JP); Hiroshi Makino, Musashino (JP); Takafumi Sakai, Hino (JP); Eiji Ishikawa, Yokohama (JP); Kenji Oishi, Tama (JP)

(73) Assignee: KABUSHIKI KAISHA YAKULT HONSHA, Tokyo (JP)

( * ) Notice: Subject to any disclaimer, the term of this patent is extended or adjusted under 35 U.S.C. 154(b) by 109 days.

(21) Appl. No.: 14/239,409

(22) PCT Filed: Aug. 31, 2012

(86) PCT No.: PCT/JP2012/072219
§ 371 (c)(1),
(2), (4) Date: Feb. 18, 2014

(87) PCT Pub. No.: WO2013/031973
PCT Pub. Date: Mar. 7, 2013

(65) Prior Publication Data
US 2014/0212879 A1    Jul. 31, 2014

(30) Foreign Application Priority Data
Sep. 1, 2011    (JP) .................... 2011-190706

(51) Int. Cl.
*C12Q 1/68*    (2006.01)
*C12P 19/34*    (2006.01)
*C07H 21/04*    (2006.01)

(52) U.S. Cl.
CPC ..................................... *C12Q 1/689* (2013.01)

(58) Field of Classification Search
None
See application file for complete search history.

(56) References Cited

U.S. PATENT DOCUMENTS

| 2009/0208948 A1 | 8/2009 | Paquette et al. |
| 2010/0233717 A1 | 9/2010 | Miller et al. |
| 2011/0287965 A1 | 11/2011 | Tsang et al. |

FOREIGN PATENT DOCUMENTS

| JP | 2003 164282 | 6/2003 |
| JP | 2010 537648 | 12/2010 |
| WO | WO 2009/030031 A1 | 3/2009 |
| WO | 2009 061752 | 5/2009 |
| WO | WO 2010/062897 A1 | 6/2010 |

OTHER PUBLICATIONS

GenBank Accession No. AY238985 [Letourneur et al., public availability 2003, retrieved on-line at http://www.ncbi.nlm.nih.gov/nuccore/AY238985, retrieval date: Nov. 17, 2015].*

Combined Chinese Office Action and Search Report issued Sep. 24, 2014 in Patent Application No. 201280042806.6 with English Translation and English Translation of Category of Cited Documents.
Ying Cheng et al., "Primary Study on the Gene Typing, Molecular Characteristics of Virulence and Resistance Associated Gene of 12 *Clostridium difficile* Clinical Isolates in China", Chinese Journal of Zoonoses, vol. 25, No. 5,Dec. 31, 2009, pp. 401-405.
Extended Search Report issued Feb. 6, 2015 in European Patent Application No. 12828007.0.
C.W. Knetsch, et al., "Comparison of real-time PCR techniques to cytotoxigenic culture methods for diagnosing Clostridium difficile infection", Journal of Clinical Microbiology. American Society for Microbiology, US, vol. 1. 49, No. 1. Jan. 1, 2011, pp. 227-231, XP008134700.
F. Barbut et al., "Rapid diagnosis of 1-10Clostridium difficile infection by multiplex real-time PCR.",European Journal of Clinical Microbiology & Infectious Diseases : Official Publication of the European Society of Clinical Microbiology Oct. 2011, vol. 1. 30. No. 10, Apr. 13, 2011, pp. 1279-1285. XP002734779.
Hiroyuki Kubota, et al., "Development of TaqMan-Based Quantitative PCR for Sensitive and Selective Detection of Toxigenic Clostridium difficile in Human Stools", PLOS ONE, vol. 1. 9. No. 10., Oct. 31, 2014, 3 Pages (e111684). XP055163064.
Boer, R.F., et al., "Evaluation of a rapid molecular screening approach for the detection of toxigenic Clostridium difficile in general and subsequent identification of the *tcd*C Δ117 mutation in human stools", Jounal of Microbiological Methods, vol. 83, pp. 59-65, (2010).
Belanger, S.D., et al., "Rapid Detection of Clostridium difficile in Feces by Real-Time PCR", Journal of Clinical Microbiology, vol. 41, No. 2, pp. 730-734, (Feb. 2003).
Matsuda, K., et al., "Determination of Clostridium difficile in Fecal Samples from Healthy Adults through Quantitative RT-PCR", Japanese Journal of Bacteriology, vol. 63, No. 1, p. 166, 3-E-27/P43, (2008) (with partial English translation).
Rinttila, T., et al., "Development of an extensive set of 16S rDNA-targeted primers for quantification of pathogenic and indigenous bacteria in faecal samples by real-time PCR", Journal of Applied Microbiology, vol. 97, pp. 1166-1177, (2004).
Rupnik, M., et al., "Clostridium difficile infection: new developments in epidemiology and pathogenesis", Nat. Rev. Microbiol., vol. 7, pp. 526-536, (Jul. 2009).

(Continued)

*Primary Examiner* — Young J Kim
(74) *Attorney, Agent, or Firm* — Oblon, McClelland, Maier & Neustadt, L.L.P (57) ABSTRACT

Provided are an oligonucleotide which realizes specific and highly sensitive detection of toxigenic *C. difficile*, and a method for detecting toxigenic *C. difficile*, the method employing the oligonucleotide.
1) A primer pair containing an oligonucleotide having a nucleotide sequence represented by SEQ ID NO: 1, and an oligonucleotide having a nucleotide sequence represented by SEQ ID NO: 2; or a primer pair having complementary sequences to the nucleotide sequences. 2) A primer pair containing an oligonucleotide having a nucleotide sequence represented by SEQ ID NO: 4, and an oligonucleotide having a nucleotide sequence represented by SEQ ID NO: 5; or a primer pair having complementary sequences to the nucleotide sequences.

3 Claims, 2 Drawing Sheets (56) References Cited

OTHER PUBLICATIONS

Houser, B. A., et al., "Real-Time Multiplex Polymerase Chain Reaction Assay for Rapid Detection of Clostridium difficile Toxin-Encoding Strains", Foodborne Pathogens and Disease, vol. 7, No. 6, pp. 719-726, (2010).

Sloan, L. M., et al., "Comparison of Real-Time PCR for Detection of the tcdC Gene with Four Toxin Immunoassays and Culture in Diagnosis of Clostridium difficile Infection" Journal of Clinical Microbiology, vol. 46, No. 6, pp. 1996-2001, (Jun. 2008).

Written Opinion of the International Searching Authority Issued Oct. 23, 2012 in PCT/JP12/072219 Filed Aug. 31, 2012.

International Search Report Issued Oct. 23, 2012 in PCT/JP12/072219 Filed Aug. 31, 2012.

* cited by examiner

METHOD FOR DETECTING TOXIN-PRODUCING *CLOSTRIDIUM DIFFICILE*

CROSS REFERENCE TO RELATED APPLICATIONS

The present application is a 35 U.S.C. §371 national stage patent application of International patent application PCT/JP2012/072219, filed on Aug. 31, 2012, published as WO/2013/031973 on Mar. 7, 2013, the text of which is incorporated by reference, and claims the benefit of the filing date of Japanese application no. 2011-190706, filed on Sep. 1, 2011, the text of which is also incorporated by reference.

TECHNICAL FIELD

The present invention relates to an oligonucleotide for detecting toxigenic *Clostridium difficile*; and to a method for detecting toxigenic *Clostridium difficile*, the method employing the oligonucleotide.

BACKGROUND ART

*Clostridium difficile* (hereinafter may be referred to as "*C. difficile*") is a sporulating Gram-positive bacillus which produces an exotoxin pathogenic to human. In recent years, *C. difficile*-associated diarrhea (CDAD) caused by this bacterium has become a serious problem (Non-Patent Document 1). Specifically, overuse of antibiotics, anticancer agents, etc. causes damage to normal intestinal flora, and the thus-grown *C. difficile* produces toxins TcdA and TcdB, to thereby develop symptoms such as diarrhea. As has been known, *C. difficile* is excreted in feces from the infected individual, and other individuals are infected with *C. difficile* through the mouth or mucosa thereof via, for example, instruments or hands.

The pathogenicity of *C. difficile* is generally attributed to two toxins TcdA and TcdB belonging to the large clostridial toxins (LCTs) family. Strains of *C. difficile* are roughly classified, according to the difference in toxicity therebetween, into a type of TcdA production and TcdB production (A+B+), a type of no TcdA production and TcdB production (A−B+), and a type of no toxin production (A−B−). The toxin production system of *C. difficile* is considered to include tcdA and tcdB, and a pathogenic locus formed by tcdC, tcdR, and tcdE which encode the regulatory factors of tcdA and tcdB. As has been reported, when tcdC which negatively controls toxin production is deleted, production of the toxins TcdA and TcdB is enhanced.

Therefore, selective detection of only toxigenic *C. difficile* strains (A+B+ and A−B+) is clinically important for diagnosis of a *Clostridium difficile* infection (CDI) such as CDAD.

Hitherto, it has been reported that several primers targeting the toxin genes tcdA and tcdB are employed for detection of toxigenic *C. difficile*, and the genes can be detected in DNA extracted from feces by means of these primers (Non-Patent Documents 2 to 4 and Patent Document 1).

However, since the number of *C. difficile* cells is small in the healthy human bowel, detection of toxigenic strains in feces by PCR requires establishment of a detection system having high specificity and detection sensitivity. Thus, conventional techniques are not satisfactory from this viewpoint.

CITATION LIST

Patent Document

Patent Document 1: JP-A-2003-164282

Non-Patent Document

Non-Patent Document 1: Rupnik, M., M. H. Wilcox, and D. N. Gerding., Nat. Rev. Microbiol. 2009, 7: 526-36

Non-Patent Document 2: Belanger, S. D., M. Boissinot, N. Clairoux, F. J. Picard, and M. G. Bergeron., J. Clin. Microbiol. 2003, 41: 730-4

Non-Patent Document 3: Houser, B. A., A. L. Hattel, and B. M. Jayarao., Foodborne Pathog. Dis. 2010, 7: 719-26

Non-Patent Document 4: Sloan, L. M., B. J. Duresko, D. R. Gustafson, and J. E. Rosenblatt., J. Clin. Microbial. 2008, 46: 1996-2001

SUMMARY OF THE INVENTION

Problems to be Solved by the Invention

An object of the present invention is to provide an oligonucleotide which realizes specific and highly sensitive detection of toxigenic *C. difficile*. Another object of the present invention is to provide a method for detecting toxigenic *C. difficile*, the method employing the oligonucleotide.

Means for Solving the Problems

In order to solve the aforementioned problems, the present inventors have found that toxigenic *C. difficile* can be specifically detected at high sensitivity by amplifying and assaying the tcdA gene and the tcdB gene by means of a specific oligonucleotide designed through alignment of tcdA gene sequences of 20 strains, tcdB gene sequences of 22 strains, the nucleotide sequence of tcsL (i.e., the toxin gene of *Clostridium sordelii*), the nucleotide sequence of tcnA (i.e., the toxin gene of *Clostridium novyi*), and the nucleotide sequence of tcpL (i.e., the toxin gene of *Clostridium perfringens*).

The present invention provides the following 1) to 10).

1) A primer pair comprising an oligonucleotide having a nucleotide sequence represented by SEQ ID NO: 1, and an oligonucleotide having a nucleotide sequence represented by SEQ ID NO: 2; or a primer pair having complementary sequences to the nucleotide sequences.

2) An oligonucleotide probe having a nucleotide sequence represented by SEQ ID NO: 3; or an oligonucleotide probe having a complementary sequence to the nucleotide sequence.

3) The oligonucleotide probe according to 2) above, wherein a fluorescent substance is bound to the 5' end of the oligonucleotide, and a quencher substance is bound to the 3' end thereof.

4) An oligonucleotide set for use in real-time PCR comprising a primer pair as recited in 1) above, and an oligonucleotide probe as recited in 3) above.

5) A primer pair comprising an oligonucleotide having a nucleotide sequence represented by SEQ ID NO: 4, and an oligonucleotide having a nucleotide sequence represented by SEQ ID NO: 5; or a primer pair having complementary sequences to the nucleotide sequences.

6) An oligonucleotide probe having a nucleotide sequence represented by SEQ ID NO: 6; or an oligonucleotide probe having a complementary sequence to the nucleotide sequence.

7) The oligonucleotide probe according to 6) above, wherein a fluorescent substance is bound to the 5' end of the oligonucleotide, and a quencher substance is bound to the 3' end thereof.

8) An oligonucleotide set for use in real-time PCR comprising a primer pair as recited in 5) above, and an oligonucleotide probe as recited in 7) above.

9) A method for detecting toxigenic *C. difficile*, comprising a step of carrying out PCR by using, as a template, DNA extracted from human feces, and an oligonucleotide set as recited in 4) or 8) above; and a step of assaying an amplified product through measurement of fluorescence.

10) A method for calculating a ratio of the number of toxigenic *C. difficile* cells and/or non-toxigenic *C. difficile* cells to the total number of *C. difficile* cells contained in human feces, the method comprising a step of carrying out PCR by using, as a template, DNA extracted from the human feces, an oligonucleotide set as recited in 4) and/or 8) above, and an oligonucleotide set for use in real-time PCR containing the following primer pair (a) or both the following primer pair (a) and oligonucleotide probe (b):

(a) a primer pair comprising an oligonucleotide having a nucleotide sequence represented by SEQ ID NO: 7, and an oligonucleotide having a nucleotide sequence represented by SEQ ID NO: 8; or a primer pair having complementary sequences to the nucleotide sequences; and (b) an oligonucleotide probe having a nucleotide sequence represented by SEQ ID NO: 9; or an oligonucleotide probe having a complementary sequence to the nucleotide sequence, wherein a fluorescent substance is bound to the 5' end of the oligonucleotide, and a quencher substance is bound to the 3' end thereof; and a step of assaying an amplified product through measurement of fluorescence.

Effects of the Invention

According to the oligonucleotide and toxigenic *C. difficile* detection method of the present invention, toxigenic *C. difficile* contained in feces can be specifically detected at high sensitivity. Therefore, according to the present invention, a toxigenic *C. difficile* infection can be readily and correctly diagnosed, and the detection frequency of a toxigenic *C. difficile* strain in feces from a healthy adult can be readily examined. In addition, the ratio of the number of toxigenic *C. difficile* cells or non-toxigenic *C. difficile* cells to the total number of *C. difficile* cells contained in the feces can be calculated by counting the total number of *C. difficile* cells.

MODES FOR CARRYING OUT THE INVENTION

The primer pair of the present invention encompasses (1) a primer pair for amplifying the tcdA gene, and (2) a primer pair for amplifying the tcdB gene.

The tcdA-gene-amplifying primer pair (1) contains a first primer; i.e., an oligonucleotide having the nucleotide sequence (5'-CAGTCGGATTGCAAGTAATTGACAAT-3' (tcdA-F)) represented by SEQ ID NO: 1, and a second primer; i.e., an oligonucleotide having the nucleotide sequence (5'-AGTAGTATCTACTACCATTAACAGTCTGC-3' (tcdA-R)) represented by SEQ ID NO: 2. The first primer can be employed as a forward primer for a nucleic acid amplification reaction such as PCR (polymerase chain reaction), and the second primer can be employed as a reverse primer in combination with the first primer for the nucleic acid amplification reaction.

Strains of *C. difficile* are roughly classified into a type of TcdA production and TcdB production (A+B+), a type of no TcdA production and TcdB production (A−B+), and a type of no toxin production (A−B−). As has been known, the presence or absence of the tcdA toxin gene does not necessarily correspond to the presence or absence of TcdA toxin production. When a conventionally known tcdA-gene-amplifying primer is employed, in many cases, not only A+B+ type strains, but also A−B+ type strains are detected. That is, a method employing such a primer fails to detect only TcdA toxin-producing bacteria (see Example 2 (3)). In contrast, when the primer pair of the present invention containing the first and second primers is employed, as shown in Table 3, only tcdA for A+B+ type strains is amplified, but tcdA for A−B+ type strains is not amplified. That is, when the tcdA-gene-amplifying primer pair of the present invention is employed, TcdA toxin-producing *C. difficile* strains (i.e., only A+B+ type strains) can be reliably detected (see Examples 2 (2) and (3)).

The tcdB-gene-amplifying primer pair (2) contains a third primer; i.e., a primer having the nucleotide sequence (5'-TACAAACAGGTGTATTTAGTACAGAAGATGGA-3' (tcdB-F)) represented by SEQ ID NO: 4, and a fourth primer; i.e., a primer having the nucleotide sequence (5'-CACCTATTTGATTTAGMCCTTTAAAAGC-3' (tcdB-R)) represented by SEQ ID NO: 5. The third primer can be employed as a forward primer for a nucleic acid amplification reaction, and the fourth primer can be employed as a reverse primer in combination with the third primer for the nucleic acid amplification reaction.

When this primer pair is employed, the tcdB gene can be reliably amplified, and TcdB toxin-producing *C. difficile* strains (i.e., both A+B+ type strains and A−B+ type strains) can be reliably detected (Table 3).

The oligonucleotide probe of the present invention encompasses (1) a probe which specifically hybridizes to the tcdA gene, and (2) a probe which specifically hybridizes to the tcdB gene.

The probe (1) which specifically hybridizes to the tcdA gene is an oligonucleotide (first probe) having the nucleotide sequence (5'-TTGAGATGATAGCAGTGTCAGGATTG-3' (tcdA-P)) represented by SEQ ID NO: 3, and the first probe specifically binds to a region amplified by the aforementioned primer pair containing the first and second primers. Meanwhile, the probe (2) which specifically hybridizes to the tcdB gene is an oligonucleotide (second probe) having the nucleotide sequence (5'-TTTKCCAGTAAAATCAATTGCTTC-3' (tcdB-P)) represented by SEQ ID NO: 6, and the second probe specifically binds to a region amplified by the aforementioned primer pair containing the third and fourth primers.

When the 5' end of the oligonucleotide probe is modified with a fluorescent substance such as FAM (carboxyfluorescein) or TET (tetrachlorocarboxyfluorescein), and the 3' end thereof is modified with a quencher substance such as TAMRA (carboxytetramethylrhodamine) or BHQ-1 (black hole quencher-1), the thus-modified oligonucleotide (so-called Taqman probe) can be employed for, for example, carrying out real-time PCR.

Specifically, the modified first probe can be employed, in combination with the aforementioned primer pair containing the first and second primers, in an oligonucleotide set for use in amplifying and assaying the tcdA gene by real-time PCR. Meanwhile, the modified second probe can be employed, in combination with the aforementioned primer pair containing the third and fourth primers, in an oligonucleotide set for use in amplifying and assaying the tcdB gene by real-time PCR.

The oligonucleotide of the present invention encompasses, in addition to the oligonucleotides having the nucleotide sequences represented by SEQ ID NOs: 1 to 6, an oligonucleotide having a complementary sequence to each of the nucleotide sequences. Specifically, the present invention encompasses a primer pair having complementary sequences to the nucleotide sequences represented by SEQ ID NOs: 1 and 2; an oligonucleotide probe having a complementary sequence to the nucleotide sequence represented by SEQ ID No: 3; a primer pair having complementary sequences to the nucleotide sequences represented by SEQ ID NOs: 4 and 5; and an oligonucleotide probe having a complementary sequence to the nucleotide sequence represented by SEQ ID No: 6.

The oligonucleotide of the present invention also encompasses an oligonucleotide which has a nucleotide sequence prepared through deletion, substitution, addition, or insertion of one or two nucleotides in any of the nucleotide sequences represented by SEQ ID NOs: 1 to 6 or in a complementary sequence to the nucleotide sequence, and which functions as a primer or a probe similarly to any of the nucleotide sequences represented by SEQ ID NOs: 1 to 6 or a nucleotide sequence complementary thereto.

The oligonucleotide of the present invention can be readily produced through a known chemical synthesis method.

TcdA toxin-producing *C. difficile* or TcdB toxin-producing *C. difficile* can be detected by carrying out a nucleic acid amplification reaction through use, as a template, of DNA extracted from human feces, and each of the aforementioned primer pairs of the present invention (preferably, in combination with each of the aforementioned oligonucleotide probes), and by assaying the thus-amplified product. This detection method includes determination of the presence or absence of *C. difficile*, and quantification of *C. difficile*. This quantification includes counting of the number of bacterial cells.

The number of TcdA toxin-producing *C. difficile* cells or TcdB toxin-producing *C. difficile* cells contained in feces can be determined by employing each of the aforementioned primer pairs of the present invention (preferably, in combination with each of the aforementioned oligonucleotide probes). In addition, when the total number of *C. difficile* cells is determined by use of the primer pairs in combination with a *C. difficile*-specific primer or probe, detailed data on *C. difficile* contained in feces (in bowel) can be obtained; i.e., the ratio of the number of toxigenic *C. difficile* cells (i.e., the number of A+B+ type strain cells, the number of A−B+ type strain cells, or the total number of A+B+ type strain cells and A−B+ type strain cells) or the number of non-toxigenic *C. difficile* cells (i.e., the number of A−B− type strain cells) to the total number of *C. difficile* cells (i.e., the total number of A+B+ type strain cells, A−B+ type strain cells, and A−B− type strain cells) can be calculated.

Examples of the *C. difficile*-specific primer or probe include an oligonucleotide set for use in real-time PCR containing the following primer pair (a) or both the following primer pair (a) and oligonucleotide probe (b):

(a) a primer pair comprising an oligonucleotide having a nucleotide sequence represented by SEQ ID NO: 7, and an oligonucleotide having a nucleotide sequence represented by SEQ ID NO: 8; or a primer pair having complementary sequences to the nucleotide sequences; and (b) an oligonucleotide probe having a nucleotide sequence represented by SEQ ID NO: 9; or an oligonucleotide probe having a complementary sequence to the nucleotide sequence, wherein a fluorescent substance is bound to the 5' end of the oligonucleotide, and a quencher substance is bound to the 3' end thereof.

The primer pair (a) contains a fifth primer; i.e., an oligonucleotide having the nucleotide sequence (5'-GCAAGT-TGAGCGATTTACTTCGGT-3' (CD16SrRNA-F)) represented by SEQ ID NO: 7, and a sixth primer; i.e., an oligonucleotide having the nucleotide sequence (5'-GTACTGGCTCACCTTTGATATTYAAGAG-3' (CD16SrRNA-R)) represented by SEQ ID NO: 8. The fifth primer can be employed as a forward primer for a nucleic acid amplification reaction, and the sixth primer can be employed as a reverse primer in combination with the fifth primer for the nucleic acid amplification reaction.

The oligonucleotide probe (b) is an oligonucleotide (third probe) having the nucleotide sequence (5'-TGCCTCT-CAAATATATTATCCCGTATTAG-3' (CD16SrRNA-P)) represented by SEQ ID NO: 9, and the third probe specifically binds to a region amplified by the aforementioned primer pair containing the fifth and sixth primers. When the 5' end of the oligonucleotide probe is modified with a fluorescent substance such as FAM or TET, and the 3' end thereof is modified with a quencher substance such as TAMRA or BHQ-1, the thus-modified oligonucleotide (so-called Taqman probe) can be employed for, for example, carrying out real-time PCR.

The aforementioned oligonucleotide (a) or (b) also encompasses an oligonucleotide which has a nucleotide sequence prepared through deletion, substitution, addition, or insertion of one or two nucleotides in any of the nucleotide sequences represented by SEQ ID NOs: 7 to 9 or in a complementary sequence to the nucleotide sequence, and which functions as a primer or a probe similarly to any of the nucleotide sequences represented by SEQ ID NOs: 7 to 9 or a nucleotide sequence complementary thereto.

Examples of the sample employed for determining, for example, the presence of a microorganism of interest or the amount of the microorganism include samples derived from living organisms, such as conjunctival swab, calculus, plaque, sputum, pharyngeal swab, saliva, nasal discharge, broncho-alveolar lavage fluid, pleural fluid, gastric juice, gastric lavage fluid, urine, cervical mucus, vaginal discharge, skin lesion, feces, blood, ascitic fluid, tissue, spinal fluid, synovial fluid, and affected area swab; and subjects which may contain the microorganism, such as foods, drugs, cosmetics, intermediate processed materials of foods, drugs, or cosmetics, microorganism cultures, plants, soil, activated sludge, and drainage water. No particular limitation is imposed on the subject-derived sample, so long as the sample can indicate the presence of a microorganism of interest in the subject or the amount of the microorganism contained in the subject. The subject-derived sample may be, for example, a mixture containing a nucleotide contained in the subject, and a mixture containing DNA contained in the subject. Preferably, the subject-derived sample is a mixture containing DNA contained in the subject, from the viewpoint that the sample is employed in PCR.

Extraction of DNA from human feces may be carried out through a technique similar to that employed in conventional genomic DNA preparation. For example, DNA may be appropriately extracted from the entirety or a portion of the sample through a known technique after optional pretreatment of the sample by extraction, separation, or purification. After optional pretreatment through a known technique such as filtration, centrifugation, or chromatography, DNA extraction may be carried out through a general-purpose method; for example, "the physical homogenization method under stirring in the presence of glass beads, etc.," "the CTAB method," "the phenol-chloroform method (PC method)," "the magnetic bead method," or "the silica column method," or a combination of these methods. DNA extraction may be carried out by means of a commercially available kit.

In order to achieve high detection sensitivity by PCR, DNA is preferably extracted at high concentration. However, since a nucleic acid extract from feces contains a substance which inhibits PCR, preferably, there is obtained high-purity DNA from which such a PCR-inhibiting substance has been removed as much as possible. For this purpose, particularly preferably, there is employed FastDNA SPIN Kit for Feces (MP Biomedicals) which realizes extraction of high-purity DNA at high concentration.

No particular limitation is imposed on the nucleic acid amplification method employed, and a known method utilizing the PCR principle may be carried out. Examples of the nucleic acid amplification method include PCR, LAMP (Loop-mediated isothermal Amplification), ICAN (Isothermal and Chimeric primer-initiated Amplification of Nucleic acids), RCA (Rolling Circle Amplification), LCR (Ligase Chain Reaction), and SDA (Strand Displacement Amplification).

Detection of an amplified product produced through nucleic acid amplification reaction may be carried out by known means which can specifically recognize the amplified product. For example, dNTP incorporated during amplification reaction may be caused to react with a labeling substance such as a radioisotope, a fluorescent substance, or a luminescent substance, and the thus-labeled product may be detected. Observation of the amplified product containing the labeled dNTP may be carried out through any method known in the art for detecting the aforementioned labeled product. When, for example, the labeling substance employed is a radioisotope, radioactivity may be determined by means of, for example, a liquid scintillation counter or a γ-counter. Meanwhile, when the labeling substance employed is a fluorescent substance, fluorescence may be detected by means of, for example, a fluorescence microscope or a fluorescence plate reader.

The nucleic acid amplification method employed in the present invention is preferably real-time PCR for real-time monitoring and analysis of the amount of nucleic acid amplified by PCR, from the viewpoints of rapidity and quantitative determination. The real-time PCR technique may be a method generally employed in the art; for example, the TaqMan probe method, the intercalater method, or the cycling probe method. In the present invention, the TaqMan probe method is particularly preferably employed.

In the TaqMan probe method, an oligonucleotide (TaqMan probe) having a 5' end modified with a fluorescent substance (e.g., FAM) and a 3' end modified with a quencher substance (e.g., TAMRA) is added to a PCR reaction system.

In the present invention, as described above, the modified first or second probe can be employed as a TaqMan probe. The TaqMan probe specifically hybridizes to template DNA in an annealing step of the PCR reaction. Since the quencher substance is provided on the probe, even when the probe is irradiated with excitation light, generation of fluorescence is suppressed. When, in an elongation step, the TaqMan probe hybridized to the template is degraded by means of the 5' to 3' exonuclease activity of the Taq DNA polymerase, the fluorescent substance is liberated from the probe, and fluorescence is generated as a result of release from suppression by the quencher substance.

No particular limitation is imposed on the PCR conditions, and optimal conditions may be determined in association with a PCR apparatus employed. For example, PCR conditions are as follows.

1) Thermal denaturation of double-stranded DNA to single-stranded DNA: heating generally at about 93 to about 95° C. generally for about 10 seconds to about one minute.

2) Annealing: heating generally at about 50 to about 60° C. generally for about 10 seconds to about one minute.

3) DNA elongation: heating generally at about 70 to about 74° C. generally for about 30 seconds to about five minutes.

In this case, annealing and DNA elongation may be carried out simultaneously rather than separately.

The tcdA gene or tcdB gene of interest can be amplified to a detectable extent by generally carrying out the aforementioned reaction including the steps 1) to 3) for about 30 to about 50 cycles.

The TaqMan probe concentration of the reaction mixture is preferably about 100 to about 1,000 nM, from the viewpoint of sensitivity.

In the case where there is employed the intercalater method in which a reagent (fluorescent intercalater) which generates fluorescence through binding to double-stranded DNA is added to a PCR reaction system, PCR may be carried out in the presence of a known reagent (fluorescent intercalater) such as SYBR Green I, SYBR Green II, SYBR Gold, oxazole yellow, thiazole orange, ethidium bromide, or Picogreen, to thereby determine the fluorescence intensity increasing in association with amplification of a target sequence.

Real-time PCR may be carried out by means of an apparatus exclusive for real-time PCR in which a thermal cycler and a spectrofluorometer are integrated together, such as ABI PRISM 7900HT sequence detection system (Applied Biosystems).

For determination of the amount of DNA, firstly, a standard DNA solution having a known concentration is diluted stepwise, and the thus-diluted solutions are subjected to PCR. The initial DNA amount is plotted along the horizontal axis, and the number of cycles at which the amount of a product amplified by PCR employing the DNA as a template reaches a certain level (i.e., threshold cycle; Ct value) is plotted along the vertical axis, to thereby prepare a calibration curve. A sample having an unknown DNA concentration is subjected to PCR under the same conditions as described above, to thereby determine Ct value. The amount of DNA of interest contained in the sample may be calculated by use of the thus-determined Ct value and the above-prepared calibration curve.

The number of cells may be determined in a manner similar to that of DNA amount determination by calculating the number of cells to the amount of DNA employed for preparation of the calibration curve. Firstly, there is determined the number of cells contained in a pure bacterial culture of a bacterial strain employed for preparation of a standard DNA solution, and DNA is extracted from the bacterial strain. On the basis of the thus-determined number of cells, the number of cells to the amount of DNA contained in a solution of the extracted DNA (standard DNA solution) can be calculated. Therefore, since the number of cells to the initial amount of DNA subjected to PCR can be calculated, when a calibration curve is prepared by plotting the number of cells along the horizontal axis, the number of cells of the microorganism of interest contained in a sample having an unknown concentration can be calculated in a manner similar to that described above.

Thus, "the amount of DNA of a microorganism of interest" or "the number of cells of the microorganism" in a sample having an unknown concentration can be determined by carrying out PCR by use of a standard DNA solution in which "the amount of DNA of the microorganism" or "the number of cells of the microorganism (corresponding to the DNA amount)" is known, together with a DNA sample having an unknown concentration, and by comparing "PCR cycle numbers" (Ct values) at which the amount of a PCR amplified product reaches a certain level. From the viewpoint of convenience, this comparison is preferably carried out by use of a calibration curve showing the relationship between "Ct value" and the "number of cells of the microorganism of interest" serving as a PCR template. Generally, the calibration curve is prepared by plotting the number of cells of the microorganism of interest along the horizontal axis, and Ct value along the vertical axis. The microorganism employed for preparation of the calibration curve may be a known bacterial strain (e.g., a type strain).

Also, the amount of DNA of a microorganism of interest contained in a sample may be determined on the basis of the efficiency of hybridization between the sample and a nucleic acid fragment which can specifically hybridize to the DNA of the microorganism.

Thus, according to the method of the present invention, TcdA toxin-producing *C. difficile* or TcdB toxin-producing *C. difficile* can be specifically detected (Example 2). Also, the DNA of *C. difficile* can be detected when $10^3$ or more cells of *C. difficile* are present in 1 g of feces (Example 3); i.e., the present invention realizes highly sensitive detection.

In addition, when the total number of *C. difficile* cells is determined by use of a *C. difficile*-specific primer set and a *C. difficile*-specific oligonucleotide probe in combination, detailed data on *C. difficile* contained in feces (in bowel) can be correctly obtained; i.e., the ratio of the number of toxigenic *C. difficile* cells and non-toxigenic *C. difficile* cells to the total number of *C. difficile* cells can be correctly calculated, which can contribute to, for example, the diagnosis or clinical study of a *C. difficile* infection.

EXAMPLES

Example 1

Detection of Toxigenic *C. difficile*

[I] Material and Method
(A) Bacterial Strain Employed and Culture Conditions

*C. difficile* DSM 1296T was purchased from Deutsche Sammlung von Mikroorganizmen und Zellkulturen GmbH (DSMZ, Germany); ATCC 43255, 43596, 43598, and 700057 were purchased from American Type Culture Collection (USA); NTCT 13307 and 13366 were purchased from Health Protection Agency (UK); and CCUG20309, 37780, and 37785 were purchased from Culture Collection University of Goteborg (Sweden). All *Clostridium* strains (except for *C. difficile*) were purchased from DSMZ.

All the bacterial strains were cultured in a modified GAM medium containing 1% glucose (Nissui Pharmaceutical Co., Ltd.) under anaerobic conditions at 37° C. for 24 hours. The number of cells contained in the bacterial culture was determined through DAPI staining.

(B) TaqMan PCR Reaction

TaqMan PCR was carried out by means of an ABI7900HT system. Takara ExTaq Hot Start Version (Takara) and Ampdirect plus (Shimadzu) were employed for the PCR. The composition of the reaction solution employed was as follows: 2×Ampdirect plus, primer F/R (0.2 µM), TaqMan probe (0.2 µM), Rox Reference Dye, ExTaq DNA polymerase (0.4 Units), and template DNA solution (5 µL) (total: 20 µL). After activation of Taq enzyme at 95° C. for 30 seconds, reaction (95° C. for 5 seconds and 56° C. for 50 seconds) was carried out for 50 cycles.

(C) Preparation of Fecal Sample for DNA Extraction

A 10% fecal suspension (w/v) (2 mL) (containing 200 mg of feces) prepared by use of RNAlater was subjected to centrifugation, and the supernatant (1 mL) was removed. Phosphate-buffered saline (PBS(−)) (1 mL) was added to the resultant product, and the mixture was stirred by vortex. Thereafter, centrifugation was carried out, and the entire supernatant was removed through decantation. PBS(−) (1 mL) was added to the resultant product, and the mixture was stirred by vortex. Thereafter, centrifugation was carried out, and the entire supernatant was removed. The resultant fecal pellets were stored at −80° C. before being used for DNA extraction.

(D) DNA Extraction

Extraction of DNA from the bacterial culture was carried out according to the method by Matsuki, et al. (Matsuki, T., K. Watanabe, J. Fujimoto, Y. Kado, T. Takada, K. Matsumoto, and R. Tanaka. 2004. Quantitative PCR with 16S rRNA-gene-targeted species-specific primers for analysis of human intestinal bifidobacteria. Appl. Environ. Microbiol. 70: 167-173).

DNA extraction from the fecal pellets was carried out by means of FastDNA SPIN Kit for Feces (MP Biomedicals). The extraction procedure will next be described in detail.

Lysing Matrix E, sodium phosphate buffer (825 µL), and Pre-lysis solution (275 µL) were added to a 2.0-mL tube containing fecal pellets (200 mg), and the mixture was stirred by vortex for 10 to 15 seconds. Then, centrifugation was carried out at 14,000×g for five minutes, and the supernatant was removed. Sodium phosphate buffer (978 µL) and MT buffer (122 µL) were added to the resultant product, and the mixture was stirred. The resultant mixture was vigorously shaken by FastPrep level 6.0 for 45 seconds, and centrifugation was carried out at 14,000×g for 15 minutes. The supernatant was recovered in a new 2.0-mL tube, and protein precipitate solution (250 µL) was added thereto, followed by vigorous shaking for mixing. The resultant mixture was allowed to stand still at 4° C. for 10 minutes, and then centrifugation was carried out at 14,000×g for two minutes. The resultant supernatant was recovered in a 15-mL tube. Binding matrix solution (1 mL) was added to the tube, and mild mixing was carried out, followed by incubation at room temperature for five minutes. Then, centrifugation was carried out at 14,000×g for two minutes, and the supernatant was removed. Thereafter, wash buffer-1 (1 mL) was added to the resultant product, and pellets were mildly resuspended through pipetting. The resultant suspension (about 600 µL) was transferred to a SPIN filter tube, and centrifugation was carried out at 14,000×g for one minute, to thereby remove a flow-through. The remaining suspension was again transferred to the SPIN filter tube, and centrifugation was carried out at 14,000×g for one minute, to thereby remove a flow-through. Wash buffer-2 (0.5 mL) was added to the resultant product, and the matrix remaining on the filter was mildly resuspended through pipetting. Thereafter, centrifugation was carried out at 14,000×g for two minutes, to thereby remove a flow-through. Centrifugation was carried out again at 14,000×g for two minutes, and the filter was transferred to a new 1.9-mL catch tube. TES (100 µL) was added to the tube, and the matrix was suspended through mild tapping. Then, centrifugation was carried out at 14,000×g for two minutes, to thereby recover a flow-through.

[II] Design of Primer and Probe

Primers and probes specific to the toxin genes tcdA and tcdB (target genes) of *C. difficile* were designed through the below-described procedure. By means of Clustal X, homology search (alignment) was carried out by use of tcdA gene sequences (*1) of 20 strains and tcdB gene sequences (*2) of 22 strains obtained from the database. TcdA and TcdB are classified as large clostridial toxins (LCTs), and they have high homology to LCTs produced by some *Clostridium* bacteria. Therefore, the gene sequences of tcsL of *Clostridium sordelii* [X82638], tcnA of *Clostridium novyi* [Z48636], and tcpL of *Clostridium perfringens* [AB262081] were also employed as controls for alignment. As a result of the alignment, the target toxin genes were found to have high homology to other genes, and the homology between the nucleotide sequences of tcdA and tcdB was found to be about 60%. Thus, a nucleotide sequence specific to each of the target toxin genes tcdA and tcdB was not found by means of software for primer preparation. Therefore, the alignment results were visually observed, and primers and probes were designed by selecting, through trial and error, regions specific to the target genes and being likely to have high conservation between bacterial strains (Table 1).

*1 GenBank accession Nos. of the tcdA gene: M30307, NC_009089, NC_013316, NC_013315, AJ011301, NZ_ADVM01000023, NZ_ABHF02000018, NZ_ABHE02000016, NZ_ABFD02000006, NZ_ABHD02000008, NZ_ABHG02000011, NZ_ABKK02000013, NZ_AAML04000007, NZ_ABKL02000008, FN668941, FN668375, FN665652, FN665653, FN665654, Y12616, and AJ132669.

*2 GenBank accession Nos. of the tcdB gene: M30307, Z23277, AJ011301, NC_009089, NC_013316, NC_013315, AF217292, NZ_ABHF02000018, NZ_ADVM01000023, NZ_ADNX01000011, NZ_ABHE02000016, NZ_ABHD02000008, NZ_ABFD02000006, NZ_ABKL02000008, NZ_ABKK02000013, NZ_ABHG02000011, NZ_AAML04000007, FN668941, FN668375, FN665652, FN665653, and FN665654.

TABLE 1

| Target gene | Primer/Probe | Sequence (5'-3') | SEQ ID NO |
|---|---|---|---|
| *C. difficile* tcdA | tcdA-F | CAGTCGGATTGCAAGTAATTGACAAT | 1 |
| | tcdA-R | AGTAGTATCTACTACCATTAACAGTCTGC | 2 |
| | tcdA-P | FAM-TTGAGATGATAGCAGTGTCAGGATTG-TAMRA | 3 |
| *C. difficile* tcdB | tcdB-F | TACAAACAGGTGTATTTAGTACAGAAGATGGA | 4 |
| | tcdB-R | CACCTATfTGATTTAGMCCTTTAAAAGC | 5 |
| | tcdB-P | FAM-TTTKCCAGTAAAATCAATTGCTTC-TAMRA | 6 |

[III] Specificity of Primer and Probe (1) Determination of Toxigenicity of *C. difficile* Strain The toxigenicities of 10 strains of *C. difficile* were examined by means of a toxin detection kit (Keul-o-test *Clostridium difficile* Complete (BioGenTechnologies)) employing immunochromatography.

Each of the strains was cultured in a BHI liquid medium under anaerobic conditions at 37° C. for four days. The culture supernatant was tested according to the protocol of the kit, and TcdA and TcdB toxigenicities were determined on the basis of the presence or absence of toxigenicity-specific bands. The results are shown in Table 2. Each strain was found to exhibit toxigenicity as shown in Table 2.

TABLE 2

| Clostridium difficile strain | Reported toxigenicity | Presence/absence of toxigenicity in pure cultured cells | |
|---|---|---|---|
| | | Tcd A | Tcd B |
| DSM 1296$^T$ | A$^+$ B$^+$ |  |  |
| ATCC 43255 | A$^+$ B$^+$ |  |  |

TABLE 2-continued

| Clostridium difficile strain | Reported toxigenicity | Presence/absence of toxigenicity in pure cultured cells | |
|---|---|---|---|
| | | Tcd A | Tcd B |
| ATCC 43596 | A⁺ B⁺ | | |
| NTCT 13307 | A⁺ B⁺ | | |
| NTCT 13366 | A⁺ B⁺ | | |
| ATCC 43598 | A⁻ B⁺ | | |
| CCUG 20309 | A⁻ B⁺ | | |
| ATCC 700057 | A⁻ B⁻ | | |
| CCUG 37780 | A⁻ B⁻ | | |
| CCUG 37785 | A⁻ B⁻ | | |

(2) Specificity (1) as Determined by TaqMan PCR

The specificity of the primer and probe sets (tcdA-F/R/P and tcdB-F/R/P) of the present invention was examined by use of 10 *C. difficile* strains (five A+B+ type strains, two A−B+ type strains, and three A−B− type strains), 10 *Clostridium* strains, and 12 enteric bacterial strains. A DNA solution extracted from pure cultured cells was subjected to TaqMan PCR (the amount of DNA per reaction: to $10^5$ cells) under the conditions described above in (B), and the presence or absence of an amplification signal was determined. The results are shown in Table 3.

are as follows: 10×PCR buffer, primer F/R (0.4 μM), dNTP (0.25 mM each), Rox Reference Dye, SYBR Green I, Taq DNA polymerase (0.25 units), and template DNA solution (5 μL) (total 20 μL). PCR was carried out for 45 cycles, each cycle consisting of 94° C. for 20 seconds, 50° C. for 30 seconds, and 74° C. for 40 seconds. When the resultant Ct value fell within a range of Ct of standard strain (DSM 1296T)±3.3, rating "+" was assigned, whereas when the resultant Ct value was 45 or more, rating "−" was assigned.

TABLE 3

| | | | Reactivity of the following primer/probe set[b] | |
|---|---|---|---|---|
| Bacterial species | Strain | Toxigenicity[a] | tcdA-F/R/P | tcdB-F/R/P |
| *Clostridium difficile* | DSM 1296[T] | A+ B+ | + | + |
| | ATCC 43255 | A+ B+ | + | + |
| | ATCC 43596 | A+ B+ | + | + |
| | NTCT 13307 | A+ B+ | + | + |
| | NTCT 13366 | A+ B+ | + | + |
| | ATCC 43598 | A− B+ | − | + |
| | CCUG 20309 | A− B+ | − | + |
| | ATCC 700057 | A− B− | − | − |
| | CCUG 37780 | A− B− | − | − |
| | CCUG 37785 | A− B− | − | − |
| *Clostridium bifermentans* | DSM 14991[T] | na | − | − |
| *Clostridium histolyticum* | DSM 2158[T] | na | − | − |
| *Clostridium innocuum* | DSM 1286[T] | na | − | − |
| *Clostridium novyi* | DSM 14992[T] | na | − | − |
| *Clostridium perfringens* | DSM 756[T] | na | − | − |
| *Clostridium ramosum* | DSM 1402[T] | na | − | − |
| *Clostridium septicum* | DSM 7534[T] | na | − | − |
| *Clostridium sordellii* | DSM 2141[T] | na | − | − |
| *Clostridium sphenoides* | DSM 632[T] | na | − | − |
| *Clostridium tertium* | DSM 2485[T] | na | − | − |
| *Blautia productus* | JCM 1471[T] | na | − | − |
| *Faecalibacterium prausnitzii* | ATCC 27768[T] | na | − | − |
| *Bacteroides vulgatus* | ATCC 8482[T] | na | − | − |
| *Bacteroides ovatus* | JCM 5824[T] | na | − | − |
| *Fusobacterium varium* | ATCC 8501[T] | na | − | − |
| *Collinsella aerofaciens* | ATCC 25986[T] | na | − | − |
| *Prevotella melaninogenica* | ATCC 25845[T] | na | − | − |
| *Veillonella parvula* | GIFU 7884[T] | na | − | − |
| *Bifidobacterium longum* | ATCC 15707[T] | na | − | − |
| *Bifidobacterium adolescentis* | ATCC 15703[T] | na | − | − |
| *Bifidobacterium catenulatum* | ATCC 27539[T] | na | − | − |
| *Lactobacillus gasseri* | DSM 20243[T] | na | − | − | a) na: Not applicable
b) +: Detection of signal, −: No detection of signal (Ct value: 50 or more), nt: Not tested As shown in Table 3, in the DSM 1296[T] strain, the amplification signals of both tcdA and tcdB were detected, which corresponded to the toxigenicity of the strain. Similarly, the amplification signal to toxigenicity was determined in other *C. difficile* strains. In contrast, in non-target bacterial strains, no signals were detected, and no primer dimer signals were determined.

(3) Specificity of Primer and Probe (2)

The specificity of the tcdA-amplifying primer (SEQ ID NOs: 39/40) selected from primer sets (J) described in Patent Document 1 was compared with that of the aforementioned primer tcdA-F/R/P of the present invention.

Specifically, the reactivity of the primer set (SEQ ID NOs: 39/40) described in Patent Document 1 to 10 *C. difficile* strains (five A+B+ type strains, two A−B+ type strains, and three A−B− type strains) was examined. A DNA solution extracted from pure cultured cells was subjected to PCR (the amount of DNA per reaction: to $10^5$ cells). PCR was carried out by use of HotStartTaq DNA polymerase (product of Qiagen). The composition of the reaction solution employed The reactivity of tcdA-F/R/P prepared in (2) above was evaluated according to the same criteria as described above. The results are shown in Table 4.

TABLE 4

| Tested bacterial strain | | tcdA-F/R/P | Primer set of Patent Document 1 (SEQ ID NOs: 39/40) |
|---|---|---|---|
| DSM 1296[T] | A+ B+ | + | + |
| ATCC 43255 | A+ B+ | + | + |
| ATCC 43596 | A+ B+ | + | + |
| NTCT 13307 | A+ B+ | + | + |
| NTCT 13366 | A+ B+ | + | + |
| ATCC 43598 | A− B+ | − | + |
| CCUG 20309 | A− B+ | − | + |
| ATCC 700057 | A− B− | − | − |
| CCUG 37780 | A− B− | − | − |
| CCUG 37785 | A− B− | − | − |

Evaluation criteria: +: Ct value within a range of Ct of standard strain (DSM 1296T) ± 3.3
−: Ct value of 45 or more In the case of the primer set (J) (SEQ ID NOs: 39/40) described in Patent Document 1, amplification of the A+B+ strain and the A−B+ strain was observed. In contrast, in the case of the tcdA-F/R/P of the present invention, amplification of the A−B+ strain was not observed. That is, it was shown that only the A+B+ strain can be reliably amplified by use of the tcdA-F/R/P.

Figure 1:
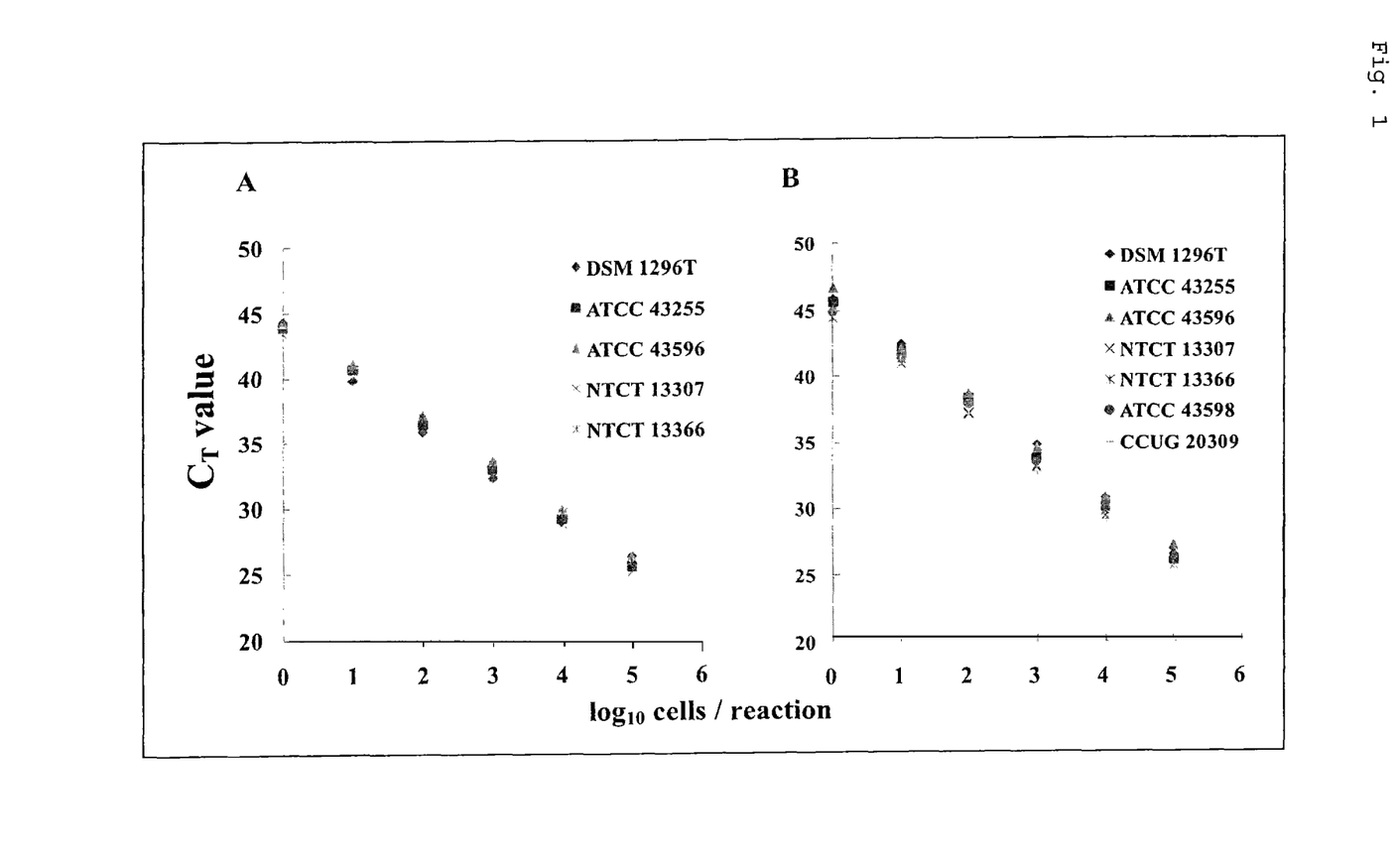
[FIG. 1]
Reactivity to target bacterial strains as determined through TaqMan PCR (A: tcdA-F/R/P, B: tcdB-F/R/P).

Next, for determination of no difference in reactivity between target bacterial strains, the calibration curves of the respective target bacterial strains were prepared and compared with one another. As a result, each of the tested target bacterial strains was found to be detected by the difference within a Ct value of 2 (four times or less as reduced to the number of cells) (FIG. 1). These data indicate that the method of the present invention can specifically and correctly detect only a bacterial strain which produces a target toxin.

Example 2

Detection of Toxigenic C. difficile
(Addition-Recovery Test)

In order to verify the lower detection limit of toxigenic C. difficile contained in feces, fecal samples from three subjects in which endogenous C. difficile had not been detected were subjected to an addition-recovery test.

Specifically, fecal samples were collected from three healthy adults who had previously been shown to have no endogenous C. difficile, and pure cultured cells of C. difficile DSM 1296$^T$ strain, which produces both TcdA and TcdB, were added to each fecal sample (number of cells per g of the sample: $10^8$, $10^7$, $10^6$, $10^5$, $10^4$, or $10^3$). The number of cells added was adjusted on the basis of the number of cells as measured through DAPI counting.

DNA extraction was carried out according to the methods described above in (C) and (D), and TaqMan PCR was carried out under the conditions described above in (B) by use of an undiluted solution of extracted DNA or a two-fold diluted solution thereof (5 μL). For formation of a standard for calibration curve preparation, the cultured cells were added to PBS(−) ($10^8$ cells per 10 mL PBS(−)) (to $10^8$ cells per g of feces), and DNA extraction was carried out in a manner similar to the case of the fecal sample. The thus-extracted standard DNA was 10-fold serially diluted (up to $10^5$-fold diluted), to thereby prepare six DNA solutions. Each of the DNA solutions (5 μL) was subjected to PCR, to thereby prepare a calibration curve. The calibration curve was employed for calculation of the number of bacterial cells in the bacterium-added fecal sample.

Figure 2:
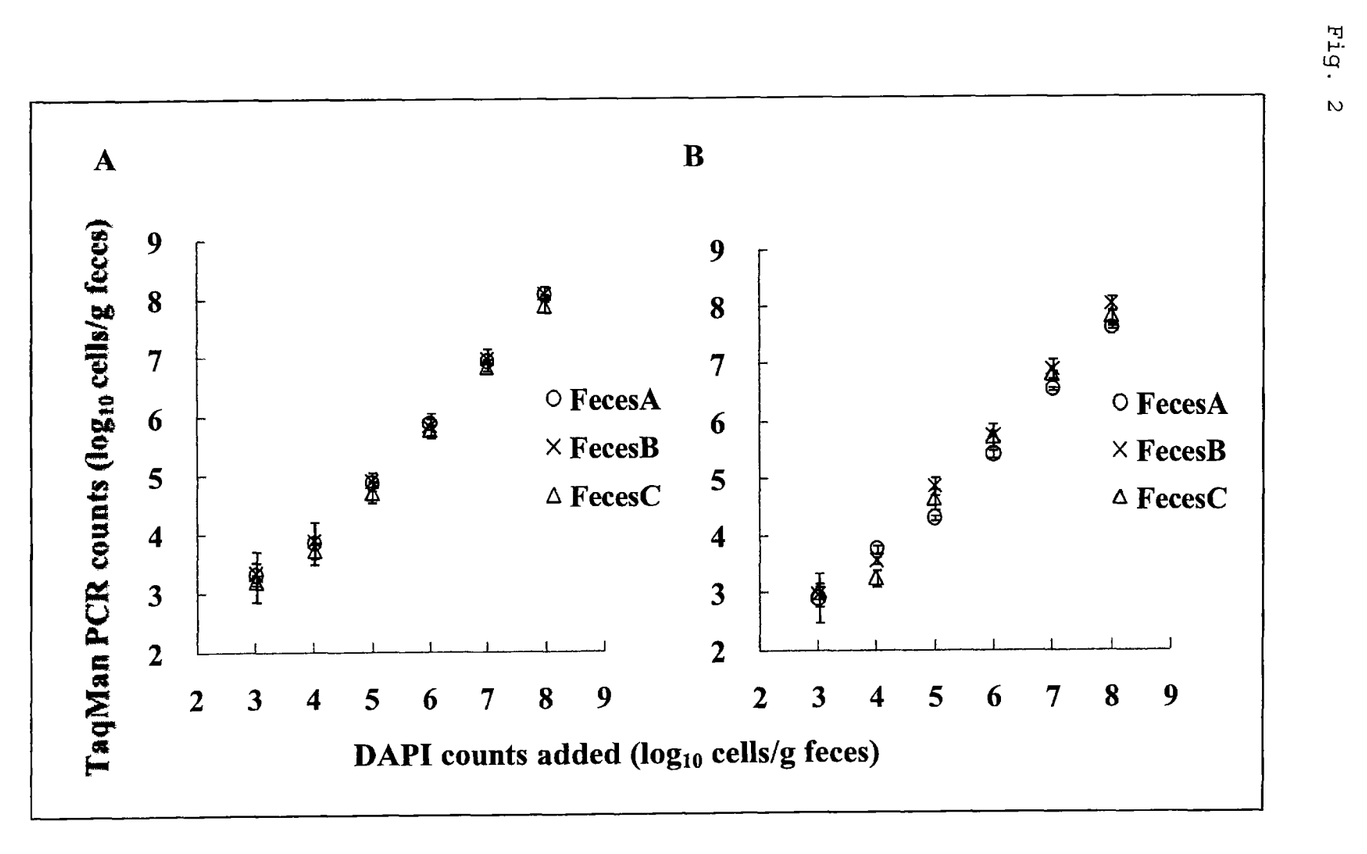
[FIG. 2]
Detection sensitivity of target bacterial strains in feces as determined through TaqMan PCR (A: tcdA-F/R/P, B: tcdB-F/R/P).

As a result, in each of the cases of tcdA-F/R/P and tcdB-F/R/P, it was found that $10^3$ bacterial cells can be detected in 1 g of feces (FIG. 2). Thus, according to the method of the present invention, target bacterial DNA can be detected at high sensitivity, and toxigenic C. difficile can be specifically quantified at high sensitivity (lower detection limit: $10^3$ cells per g of feces).

Example 3

Detection of Strain of Endogenous Enteric Bacterium

[I] Material and Method
(1) Preparation of CD16SrRNA-F/R/P

There were prepared a primer set CD16SrRNA-F and CD16SrRNA-R employed for measuring the total number of C. difficile cells, as well as a TaqMan probe CD16SrRNA-P newly designed for the amplification region (Table 5).

TABLE 5

| Primer/Probe | Sequence (5'-3') | SEQ ID NO |
|---|---|---|
| CD16SrRNA-F | GCAAGTTGAGCGATTTACTTCGGT | 7 |
| CD16SrRNA-R | GTACTGGCTCACCTTTGATATTYAAGAG | 8 |
| CD16SrRNA-P | FAM-TGCCTCTCAAATATATTATCCCGT ATTAG-TAMRA | 9 |

(2) Fecal DNA Sample

Among fecal samples collected from 102 subjects (residents and staff of a geriatric facility in Japan), 16 samples from which C. difficile had been separated through the selective culture method were selected. The DNA of each of the selected 16 fecal samples was employed for this analysis.

(3) Selective Culture Method

A frozen fecal sample was melted and suspended in a 9-fold volume of an anaerobic transport medium. The resultant suspension was mixed with an equiamount of 98% ethanol, and incubation was carried out at room temperature for 30 minutes. The ethanol-treated liquid (0.1 mL) was smeared on a cycloserine cefoxin mannitol agar (CCMA), and this medium was subjected to anaerobic culture at 37° C. for 24 hours. There was counted the number of colonies which were detected on the medium and which were regarded as C. difficile according to the characteristics and Gram staining properties.

(4) DNA Extraction

Glass beads (φ0.1 mm) (0.3 g), Tris-SDS solution (prepared through mixing of 200 mM Tris-HCl (250 mL), 80 mM EDTA (pH 9.0), and 10%, SDS (50 mL)) (300 μL), and Tris-EDTA buffer saturated phenol (500 μL) are added to a bacterial suspension (200 μL) for calibration curve preparation or a 10-fold diluted fecal liquid contained in a 2-mL screw cap tube.

The sample-containing tube is placed in a shaking homogenizer (FastPrep FP120). The tube is vigorously shaken at a power level of 5.0 for 30 seconds, to thereby homogenize cells. The tube is removed from the homogenizer, and subjected to centrifugation at 15,000 rpm for five minutes.

The resultant supernatant (400 μL) is transferred to a new 2-mL screw cap tube. Phenol/chloroform/isoamyl alcohol (25:24:1) (400 μL) is added to the supernatant, and the tube is placed in FastPrep FP120. The tube is vigorously shaken at a power level of 4.0 for 45 seconds, and subjected to centrifugation at 15,000 rpm for five minutes.

The resultant supernatant (250 μL) is transferred to a new 1.5-mL tube. 3M Na acetate (pH 5.4) (25 μL) is added to and mixed with the supernatant.

Isopropanol (300 μL) is added to the tube. Centrifugation is carried out at 15,000 rpm for five minutes. The resultant supernatant is removed through decantation. 70% Ethanol (500 μL) is added to the tube, and the tube is subjected, as is (without stirring), to centrifugation again at 15,000 rpm for five minutes. The resultant supernatant is removed through decantation.

The cap is removed, and the tube is heated at 60° C. by means of a heat block incubator for about 30 minutes for drying. Tris-EDTA buffer is added to the tube, and the mixture is stirred for uniform dissolution. The resultant product is cryopreserved at −30° C.

(5) TaqMan PCR Reaction

Reaction was carried out in a manner similar to that described in Example 1 [I] (B).

[II] Results

Toxigenic strains were detected in eight of the 16 samples (Table 6). As is clear from Table 6, enteric A+B+ type toxigenic strains are predominantly present in seven of these eight samples, since the total number of *C. difficile* cells (CD16SrRNA-F/R/P), the number of TcdA-producing *C. difficile* cells (tcdA-F/R/P), and the number of TcdB-producing *C. difficile* cells (tcdB-F/R/P), as determined through TaqMan PCR, are almost equal to one another in the seven samples.

In one sample (S-09) of the eight samples in which toxigenic strains were detected, the total number (logarithmic value) of *C. difficile* cells was considerably greater by 1.5 or more than the number (logarithmic value) of toxigenic *C. difficile* cells. The data indicate that non-toxigenic *C. difficile* is predominant (i.e., predominantly present in bowel) in the sample, and non-predominant toxigenic *C. difficile* can also be detected in the sample.

Thus, when CD16SrRNA-F/R/P, tcdA-F/R/P, and tcdB-F/R/P are employed in combination, there can be determined, through TaqMan PCR, the total number of *C. difficile* cells (the total number of A+B+ type cells, A−B+ type cells, and A−B− type cells), the number of TcdA-producing *C. difficile* (A+B+ type) cells, and the number of TcdB-producing *C. difficile* cells (the total number of A+B+ type cells and A−B+ type cells). Therefore, detailed data on *C. difficile* contained in feces (in bowel) can be correctly obtained; i.e., the total number of *C. difficile* cells, and the ratio of the number of toxigenic *C. difficile* cells and non-toxigenic *C. difficile* cells to the total number of *C. difficile* cells can be correctly calculated, which can contribute to, for example, the diagnosis or clinical study of a *C. difficile* infection.

TABLE 6

| Subject ID | Selective culture method Culture counts ($\log_{10}$ CFU/g feces) | Taq Man PCR ($\log10$ CFU/g feces) | | |
|---|---|---|---|---|
| | | CD16SrRNA-F/R/P | tcdA-F/R/P | tcdB-F/R/P |
| S-01 | 6.6 | 6.3 | 6.4 | 6.3 |
| S-02 | 6.0 | 7.0 | 7.1 | 7.0 |
| S-03 | 5.8 | 6.5 | 6.5 | 6.2 |
| S-04 | 5.0 | 7.0 | 6.9 | 6.8 |
| S-05 | 4.7 | 7.5 | 7.5 | 7.5 |
| S-06 | 4.4 | 7.7 | 7.8 | 7.8 |
| S-07 | 3.8 | 5.0 | 5.2 | 5.0 |
| S-08 | 2.9 | Not Detected | Not Detected | Not Detected |
| S-09 | 6.3 | 7.8 | 6.3 | 6.2 |
| S-10 | 5.5 | 6.4 | Not Detected | Not Detected |
| S-11 | 4.8 | 6.1 | Not Detected | Not Detected |
| S-12 | 4.8 | 6.5 | Not Detected | Not Detected |
| S-13 | 4.6 | 8.7 | Not Detected | Not Detected |
| S-14 | 4.4 | 5.6 | Not Detected | Not Detected |
| S-15 | 4.0 | 6.6 | Not Detected | Not Detected |
| S-16 | 3.4 | 5.8 | Not Detected | Not Detected |

The invention claimed is:

1. An oligonucleotide probe comprising (i) a nucleotide sequence represented by SEQ ID NO: 3; or (ii) a nucleotide sequence that is complementary to SEQ ID NO: 3, wherein a fluorescent substance is bound to the 5' end of the oligonucleotide probe, and a quencher substance is bound to the 3' end of the oligonucleotide probe.

2. An oligonucleotide set comprising:

a primer pair comprising:

(i) an oligonucleotide comprising a nucleotide sequence represented by SEQ ID NO: 1, and an oligonucleotide comprising a nucleotide sequence represented by SEQ ID NO: 2; or (ii) an oligonucleotide comprising a nucleotide sequence that is complementary to SEQ ID NO: 1, and an oligonucleotide comprising a nucleotide sequence that is complementary to SEQ ID NO: 2, and an oligonucleotide probe comprising (i) a nucleotide sequence represented by SEQ ID NO: 3; or (ii) a nucleotide sequence that is complementary to SEQ ID NO: 3, wherein a fluorescent substance is bound to the 5' end of the oligonucleotide probe, and a quencher substance is bound to the 3' end of the oligonucleotide probe.

3. A method for detecting toxigenic *C. difficile*, comprising:

performing PCR by using, as a template, DNA extracted from human feces, and the oligonucleotide set of claim 2; and assaying an amplified product through measurement of fluorescence.

* * * * *

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: primer sequence specific to tcdA gene(tcdA-F)

<400> SEQUENCE: 1
cagtcggatt gcaagtaatt gacaat                                        26

<210> SEQ ID NO 2
<211> LENGTH: 29
<212> TYPE: DNA
<213> ORGANISM: Artificial Sequence
<220> FEATURE:
<223> OTHER INFORMATION: primer sequence specific to tcdA gene(tcdA-R)

<400> SEQUENCE: 2
agtagtatct actaccatta acagtctgc                                     29

<210> SEQ ID NO 3
<211> LENGTH: 26
<212> TYPE: DNA
<213> ORGANISM: Artificial Sequence

```
<220> FEATURE:
<223> OTHER INFORMATION: probe sequence specific to tcdA gene(tcdA-P)

<400> SEQUENCE: 3
ttgagatgat agcagtgtca ggattg                                          26

<210> SEQ ID NO 4
<211> LENGTH: 32
<212> TYPE: DNA
<213> ORGANISM: Artificial Sequence
<220> FEATURE:
<223> OTHER INFORMATION: primer sequence specific to tcdB gene(tcdB-F)

<400> SEQUENCE: 4
tacaaacagg tgtatttagt acagaagatg ga                                   32

<210> SEQ ID NO 5
<211> LENGTH: 28
<212> TYPE: DNA
<213> ORGANISM: Artificial Sequence
<220> FEATURE:
<223> OTHER INFORMATION: primer sequence specific to tcdB gene(tcdB-R)

<400> SEQUENCE: 5
cacctatttg atttagmcct ttaaaagc                                        28

<210> SEQ ID NO 6
<211> LENGTH: 24
<212> TYPE: DNA
<213> ORGANISM: Artificial Sequence
<220> FEATURE:
<223> OTHER INFORMATION: probe sequence specific to tcdB gene(tcdB-P)

<400> SEQUENCE: 6
tttkccagta aaatcaattg cttc                                            24

<210> SEQ ID NO 7
<211> LENGTH: 24
<212> TYPE: DNA
<213> ORGANISM: Artificial Sequence
<220> FEATURE:
<223> OTHER INFORMATION: probe sequence specific to
      c.difficile(CD16SrRNA-F)

<400> SEQUENCE: 7
gcaagttgag cgatttactt cggt                                            24

<210> SEQ ID NO 8
<211> LENGTH: 28
<212> TYPE: DNA
<213> ORGANISM: Artificial Sequence
<220> FEATURE:
<223> OTHER INFORMATION: probe sequence specific to
      c.difficile(CD16SrRNA-R)

<400> SEQUENCE: 8
gtactggctc acctttgata ttyaagag                                        28

<210> SEQ ID NO 9
<211> LENGTH: 29
<212> TYPE: DNA
<213> ORGANISM: Artificial Sequence
<220> FEATURE:
<223> OTHER INFORMATION: probe sequence specific to
      c.difficile(CD16SrRNA-P)
```

<400> SEQUENCE: 9
tgcctctcaa atatattatc ccgtattag                    29